United States Patent [19]

Williamson

[11] Patent Number: 4,809,710
[45] Date of Patent: Mar. 7, 1989

[54] MULTILUMEN MANOMETER CATHETER

[76] Inventor: Jeffrey L. Williamson, 808 Devonshire, Champaign, Ill. 61820

[21] Appl. No.: 142,435

[22] Filed: Jan. 11, 1988

[51] Int. Cl.⁴ .............................................. A61B 5/00
[52] U.S. Cl. ..................................... 128/748; 128/780
[58] Field of Search ............................... 128/672-673, 128/674, 748, 774, 778, 780, 782

[56] References Cited

U.S. PATENT DOCUMENTS

| | | | |
|---|---|---|---|
| 3,437,088 | 4/1969 | Bielinski | 128/780 |
| 3,480,003 | 11/1969 | Crites | 128/748 X |
| 3,752,150 | 8/1973 | Harris | 128/778 |
| 4,030,481 | 6/1977 | Hill | 128/748 |
| 4,136,681 | 1/1979 | Hon | 128/748 |
| 4,214,593 | 7/1980 | Imbruce et al. | 128/780 X |
| 4,538,621 | 9/1985 | Jarczyn | 128/748 |

FOREIGN PATENT DOCUMENTS 7707275 1/1979 Netherlands .......................... 128/733

OTHER PUBLICATIONS

Ulmsten et al.; "A New Multi-Transducer Catheter for Intraluminal Pressure Recording In Vivo"; *Electromedica*, vol. 48, 1(80), pp. 9-12.

Shaw et al.; "Oesophageal Manometry by Liquid-Filled Catheters"; *Med. and Biol. Eng. and Comput.*, vol. 18, No. 4, 7-1980, pp. 488-492.

*Primary Examiner*—Max Hindenburg
*Assistant Examiner*—Angela D. Sykes
*Attorney, Agent, or Firm*—McCaleb, Lucas & Brugman

[57] ABSTRACT

A catheter for making pressure measurements in a sphincter canal. The example illustrated is for an anal sphincter canal. It has an inflation tube and water-perfusion tubes or lumens in a unitary, elongated body. A balloon or cuff is inflatable through the inflation tube. The body has a section in which the water-perfusion tubes are helically wound about the inflation tube which is centrally located. The water-perfusion tubes have side openings communicating with the lumens therewithin. These side openings are positioned along a line parallel to the longitudinal axis. Examples are shown where these side openings are located in one, two or four quadrants of the catheter surface, at different axial levels.

14 Claims, 2 Drawing Sheets

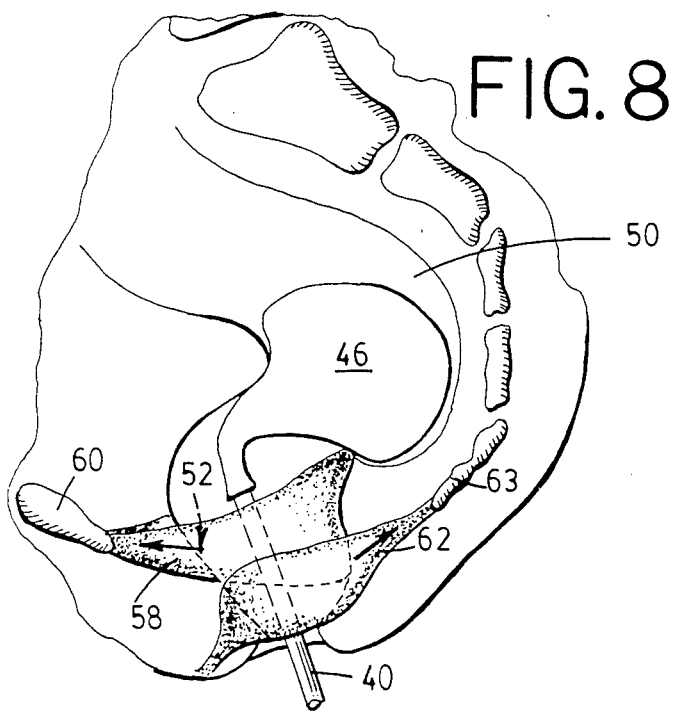
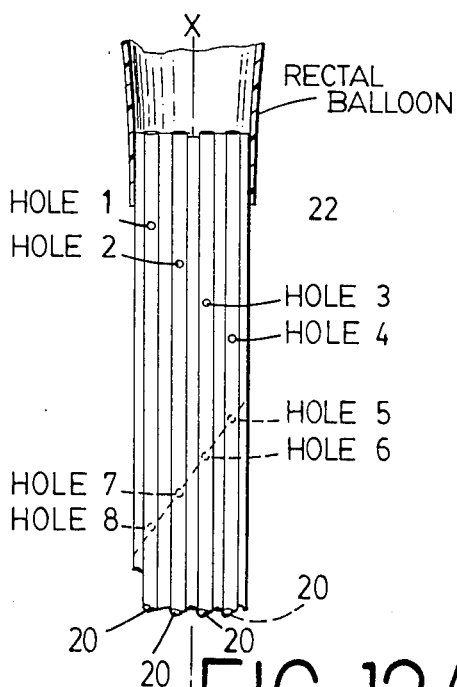
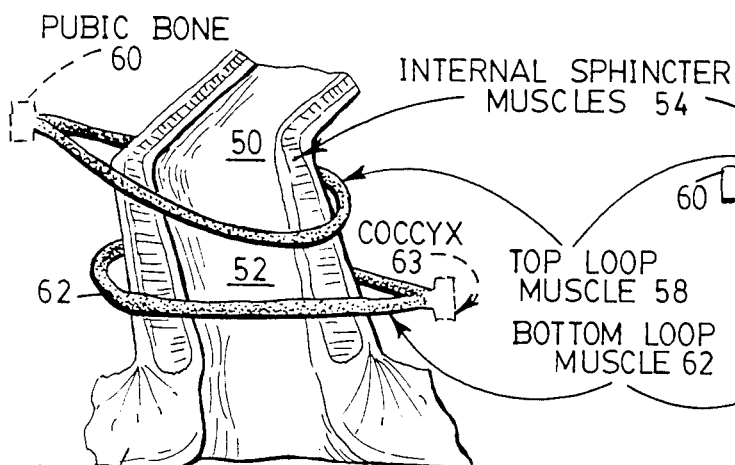
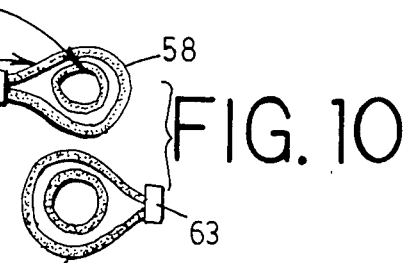
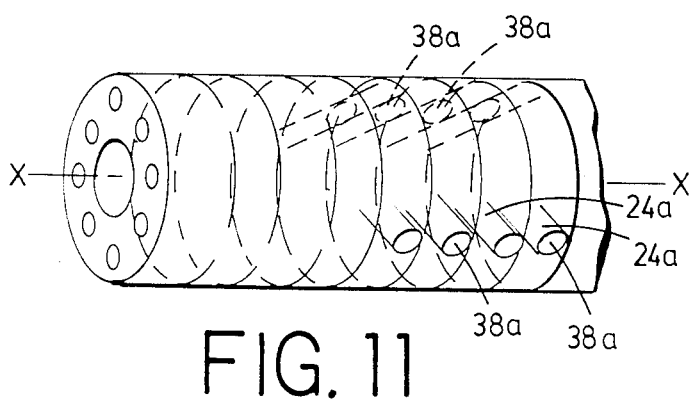
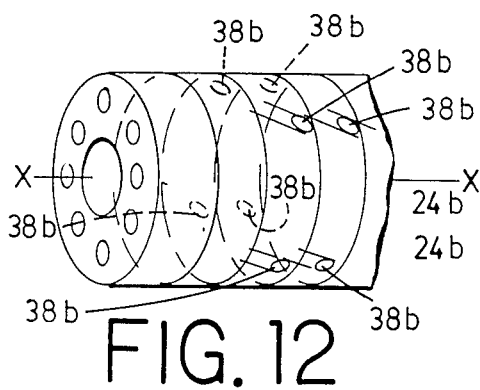

MULTILUMEN MANOMETER CATHETER

BACKGROUND OF THE INVENTION

Sphincter muscles, when contracted, close natural body openings. When they do not contract normally, unintended leakage of body fluids and solids can cause severe discomfort, pain and/or embarrassment.

Two examples are the lower esophageal sphincter muscles at the distal portion of the esophagus and the anal canal sphincter system. The esophageal sphincter muscle system acts as a barrier preventing reflux of acidic gastric contents. When it fails, there is an uncomfortable or painful acid condition in the esophagus and throat. The anal sphincter muscle system also acts as a barrier preventing uncontrolled passage of fecal contents from the rectum. The resulting fecal incontinence causes embarrassment and can severely limit a person's activities.

Fortunately, some sphincter muscle problems can be improved by surgery or by medical treatment. The anal sphincter muscle system includes both internal and external sphincter muscles. The internal muscles are involuntary and the external muscles include two major muscle groups with both voluntary and reflex responsiveness.

One of the conventional tools available for the diagnosis and also the treatment of some causes of anal incontinence is a multilumen manometric catheter for measuring the contracting pressure of the sphincter muscles around the anal canal. The conventional catheter comprises a plurality of pressure-sensing tubes (or a unitary plastic extrusion with individual lumina instead of separate tubes). These tubes or lumina extend in a circular array about a central inflation tube through which a rectal balloon at the distal end is inflated. Side openings in the water-perfusion tubes are provided at different axial levels or positions to transmit canal pressures from those different levels. Pressure readouts are obtained from coupling at the proximal ends of the tubes using a conventional hydraulic capillary infusion device, pressure transducers, and a graphic recorder.

With the catheter device and readout equipment in place, canal pressures are determined by having the patient relax, with and without the rectal balloon inflated, and also exert voluntary contraction efforts. These voluntary contraction efforts can be sustained for only short times during which multiple pressure readings at the various levels along the catheter can be read to determine which muscles are effective and to what extent.

Unfortunately, there are serious drawbacks using this procedure with conventional catheters. The pressure readings are imprecise because it is impossible to obtain instant comparative pressure readings in the same quadrant at different axial levels along the canal, and it is impossible to obtain a reliable three dimensional pressure profile at any one instant in time. The most serious drawback is that, as shown in FIG. 12A, in the pressure-sensing section of the conventional prior art catheter, the water-perfusion tubes 20 are straight and parallel to the longitudinal axis X—X. Inasmuch as there cannot be more than one side opening 22 in each straight tube, and the side openings 22 are circumferentially displaced from one another at different levels along the longitudinal axis, the only practical way they can be positioned at different levels is to arrange them in a helical line about the catheter as is shown in FIG. 12A. It is impossible to obtain a series of simultaneous pressure readings in one quadrant along any straight line parallel to the catheter axis because each pressure reading location (side-hole) 22 is offset circumferentially from adjacent pressure reading side-holes. Thus, the eight side-openings 22 shown in FIG. 12A comprise a series of holes 1, 2, 3, 4, 5, 6, 7, and 8 disposed in a helical pattern about the catheter. No two holes are at the same axial level, or in a same line parallel to the catheter axis.

Another problem in obtaining meaningful pressure readings with the conventional prior art catheter is that the sphincter muscle voluntary contraction force can be maximally generated momentarily before some weakening occurs. The catheter therefore cannot be rotated during a contraction for the purpose of taking meaningful pressure readings along any straight line parallel to the axis. Additionally, any motion of the catheter during a squeeze can set off involuntary reflex contractions which would interfere with the normal voluntary contraction pattern.

Another consideration making it impossible to obtain meaningful comparative pressure readings at different levels with the conventional straight tubes 20 shown in FIG. 12A is that the external anal sphincter muscles are asymmetric as will be described in connection with FIGS. 8, 9 and 10. They do not exert uniform contractile forces. They are loops, exerting oppositely directed lateral forces against the canal. The top loop sometimes referred to as the puborectalis and deep portion of the external sphincter, is connected anteriorly to the pubic bone and pulls the upper portion of the canal forwardly. The lower muscle group is a loop connected posteriorly to the coccyx (tail bone) and pulls the lower half of the canal rearwardly. When both muscle groups are contracted normally, pressures should maximize at an upper posterior location and at a lower anterior location and should be generally the same in anterior, posterior, right and left lateral locations at the intermediate level where the two loops overlap.

Considering the asymmetric configurations of the muscles, and the inability of a patient to voluntarily contract these muscles for any long time period, it would be advantageous if the catheter used for pressure measurements could measure pressures simultaneously, at different levels, *in the same vertical plane.*

Only one serious attempt to develop such an instrument is known. That was a multiple strain gauge instrument described in Gut, Volume 10, 1969, pages 160–163. This was a multiple electromechanical strain gauge which was unreliable and broke down after minimal use.

SUMMARY OF THE INVENTION

Accordingly, the general object of the invention is to provide an instrument capable of providing a three dimensional pressure profile in a sphincter canal by sensing and measuring canal pressures simultaneously at a plurality of sensing points located in one or more straight lines parallel to the axis in one or more quadrants, and at different, pre-determined levels.

A specific object of the invention is to provide a catheter with an elongated pressure-sensing section having a plurality of water-perfusion tubes or lumens helically oriented about the longitudinal axis, with side openings in the respective tubes or lumens located in a straight line parallel to the axis in at least one quadrant for providing simultaneous pressure readings at different levels along that line in that quadrant.

Another object is to provide such a catheter in which the pressure-sensing side openings are located in at least two opposite quadrants enabling simultaneous pressure measurements, anteriorly and posteriorly, or right and left laterally, within a sphincter canal, at multiple levels simultaneously.

Another object is to provide such a catheter in which the pressure-sensing side openings are located in four quadrants at multiple levels, enabling full, simultaneous, three-dimensional pressure profile measurements within the sphincter canal.

GENERAL DESCRIPTION OF THE DRAWINGS

FIG. 8 is a schematic view of the human anorectal body structure showing a simplified version of the double loop, asymmetric muscle system of the external anal sphincter with which the present invention is particularly useful;

FIG. 9 is a further schematic view of the double loop, asymmetric muscle system of the external anal sphincter;

FIG. 10 shows diagrammatic views of the two external sphincter system muscles;

FIGS. 11 and 12 are fragmentary, enlarged views of alternate forms of the present invention; and FIG. 12a is a view similar to FIG. 3 of the water-perfusion section of a conventional prior art catheter.

Like parts are referred to by like reference numerals throughout the figures of the drawings.

DESCRIPTION OF THE PREFERRED EMBODIMENTS

Figure 1:
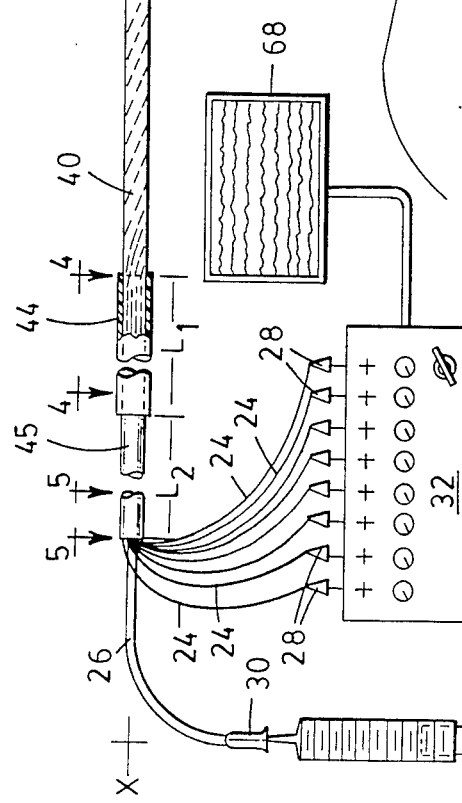
FIG. 1 is a side view of a multilumen manometric catheter illustrating a preferred form of the invention.

Referring now to the preferred embodiments shown in the drawings, FIG. 1 shows a multilumen anorectal manometer catheter illustrating one preferred form of the present invention.

It comprises an elongated plastics body having a plurality of water-perfusion tubes 24 and a central inflation tube 26. In the example shown, there are eight water-perfusion tubes 24. The eight tubes 24 are made of plastics material, for example, polyvinyl chloride, of about a size 22 gauge. The central tube 26 may be of about a size 16 gauge. Other options would include sixteen size 22 gauge water-perfusion tubes around a size 5 gauge central tube; and twelve size 22 gauge water-perfusion tubes around a size 9 gauge central tube.

Tubes 24 and 26 have Luer-type socket fittings 28 and 30 respectively at their proximal ends for connection to a capillary infusion unit 32, and to a syringe 34. Tubes 24 are closed by plugs 36 just distal of side openings 38.

The central inflation tube 26 is connected via Luer tube 30 to a source of inflation air, in this case the syringe 34.

In the embodiment shown in FIGS. 1–6, tubes 24 and 26 comprise an integral body 40 resulting from adhering them with a suitable solvent, for example, tetrahydrofurantoin. The bonded tubes are then dipped in a column of a solution of polyvinyl chloride scraps dissolved in tetrohydrofurantoin or other suitable solvent. When dried, the body will be solid except for the lumens inside the tubes which will be permanently fixed in the positions and helically angular configurations shown.

Figure 7:
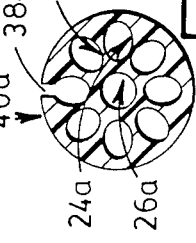
FIG. 7 is a view similar to FIG. 6 of an optional form of the invention.

As shown in FIG. 7, an optional catheter body 40a may be extended in a single, coherent body with the lumens 24a and 26a being the full equivalent of the lumens in tubes 24 and 26 respectively.

The body 40 has a water-perfusion or pressure sensing section 42 in which the water-perfusion tubes 24 are helically wound about the central tube 26 along the longitudinal axis X—X of the body 40. The tubes are fixed in this helical relationship by the plastic solvent and coating material described above. The circular array of tubes 24 comprise the external surface of the catheter body 40 in the embodiment shown in FIGS. 1–6.

Figure 3:
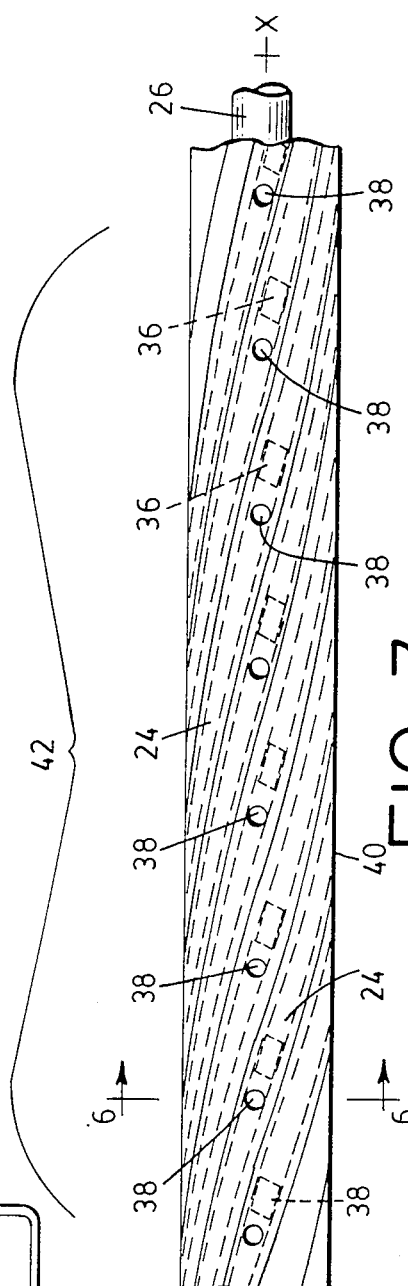
FIG. 3 is a fragmentary, enlarged view of FIG. 1 taken in the direction of arrows 3—3.
Figure 6:
FIG. 6 is a cross-section of FIG. 3, taken along line 6—6.

The side openings 38 in the water-perfusion tubes 24 provide communication between locations on the surface of the section 42 and the internal lumina of the respective tubes 24. As best shown in FIGS. 1 and 3, the side openings 38 are located at different levels along the longitudinal axis X—X. By contrast, as described above and shown in FIG. 12A, the side openings 22 in the conventional prior art catheters have been helically located about the body. By winding the tubes 24 of the present invention at a selected helical angle, or forming the lumens 24a (FIG. 7) at such a selected helical angle, the side openings 38, or 38a (FIG. 7) may be disposed at predetermined, uniform levels 0.3 to 1.0 centimeters apart along the length of the catheter body 40, or 40a.

Figure 2:
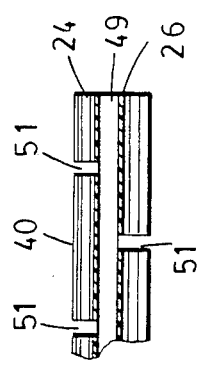
FIG. 2 is a fragmentary, enlarged view of FIG. 1 taken along line 2—2.
Figure 5:
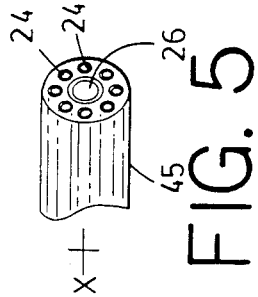
FIG. 5 is a fragmentary, enlarged view of FIG. 1, taken in the direction of arrows 5—5.
Figure 4:
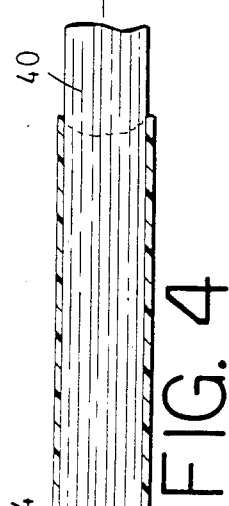
FIG. 4 is a fragmentary, enlarged view of FIG. 1, taken in the direction of arrows 4—4, with an outer portion cut away.

As shown in FIGS. 2, 4, and 5, the tubes 24 in the catheter body sections remote from the pressure-sensing section 42 may be parallel to, or at any other orientation relative to, the longitudinal axis X—X. There is no particular reason for them to be helically oriented as shown in section 42 but there would be no objection to that if it provided some manufacturing or other advantage.

As best shown in FIGS. 1 and 4, a relatively large tube 44 may be fitted over the outside of the catheter body and held in place by a shrink fit or polyvinyl chloride or other suitable cement, to serve as a handle to clamp it in place during use. Typically, the length $L_1$ of the handle may be about 12 inches. In use, it may be held by any suitable clamp mechanism (not shown) to prevent longitudinal or torsional displacement of the catheter. The proximal end portion 45 of the catheter may be any suitable length $L_2$ which may vary from a few centimeters to several centimeters.

At the distal end, just beyond the pressure-sensing section 42, a rectal distending balloon 46 may be fitted over the body 40, tightly held by threads 48, and sealed with plastics cement. As best shown in FIGS. 1 and 2, central tube 26 communicates with the rectal balloon via end opening 49 and side openings 51.

Referring now to the anorectal region shown in FIGS. 8 and 9, the rectum 50 and anal canal 52 are shown with internal sphincter muscles 54, and external sphincter muscles comprising a top loop muscle 58, sometimes called the puborectalis sling, and a bottom loop muscle 62.

These external sphincter muscles 58 and 62 comprise a "double loop system" which is anatomically and physiologically asymmetric. The top loop muscle 58 is attached anteriorly to the pubic bone 60 and pulls the top portion of the anal canal anteriorly. The bottom loop muscle 62 is attached posteriorly to the coccyx (tailbone) 63 and pulls the bottom portion of the anal canal posteriorly.

Use and operation will be described primarily in connection with FIGS. 1 and 8. With the balloon 46 initially deflated, it will be positioned in the rectum and the pressure-sensing section 40 positioned in the anal canal as shown in FIG. 8. Pressure readings may be taken at the eight points corresponding to the side openings 38. Pressure readings may be taken with the balloon 46 deflated, and other comparative readings may be taken with the balloon inflated by air through central tube 26 provided by the syringe 34. Pressure readings will be taken at the points 38 by the hydraulic capillary infusion unit 32 with pressure tranducers and recorded by a pressure recorder 68. Neither of the units 32 or 68 will be described in detail because they may be conventional and comprise no part of the present invention. An example of such hydraulic capillary infusion unit 32 is known as the Arndorfer Unit and is available from Medical Specialties, Inc., Greendale, Wis. 53129.

Pressure readings along a particular line at different levels in the anal canal may be taken in a preferred quadrant by rotating the catheter to contact the desired canal surface with the line of pressure sensing openings 38 in the preferred quadrant. Even if the patient is able to voluntarily contact the sphincter muscles for only a very short time, meaningful simultaneous pressure comparisons will be obtained along the entire length of the anal canal. Similar meaningful measurements can be obtained in other quadrants by rotating the catheter and repeating the procedure with the rectal balloon inflated or deflated. This will give a detailed pressure profile of the entire anal canal at all levels and selected quadrants.

FIG. 11 shows an optional arrangement in which the eight pressure sensing tubes 24a and eight openings 38a are arranged to provide four pressure-sensing openings 38a along a first line parallel to the longitudinal axis X—X and another four openings 38a at the same levels along another line diametrically opposite the first line. This arrangement makes it possible simultaneously to obtain two pressure readings, one anterior and the other posterior, at four separate and distinct levels along the canal.

FIG. 12 shows a further optional arrangement in which eight water-perfusion tubes 24b and eight side openings 38b are further arranged to provide two side openings in each of four quadrants, along four lines which are parallel to the axis X—X and are precisely 90 degrees circumferentially apart. This arrangement makes is possible to obtain a true and complete three dimensional pressure profile with pressure readings taken simultaneously at the anterior, posterior, lateral left, and lateral right locations within the canal and at two separate and distinct levels.

While particular examples of the present invention have been shown and described, changes and modifications may be made without departing from the broad aspects of the invention. For example, while the invention is described and shown with eight side openings 38, 38a, and 38b, more or less than eight may be used. The aim of the appended claims therefore is to cover all such changes and modifications included in the scope of the invention.

The embodiments of the invention in which an exclusive property or privilege is claimed are defined as follows:

1. A multilumen manometric catheter comprising:
   an elongated body having a plurality of lumens extending along a longitudinal axis between proximal and distal ends of the body;
   pressure transducer coupling means for the lumens at the proximal end of the body;
   said body having a pressure-sensing section at the distal end portion in which the lumens are helically oriented about the longitudinal axis;
   each of the lumens in said pressure-sensing section having a pressure-sensing side opening extending through the surface of said body adapted to sense pressure of abutting body tissue at that opening;
   each of said lumens being closed distally of the side opening therein;
   said side openings including at least one group of openings in one quadrant that are positioned along a line parallel to said longitudinal axis at predetermined levels along said axis.

2. A multilumen manometric catheter according to claim 1 in which:
   all of said pressure-sensing side openings are positioned along a single line parallel to said longitudinal axis.

3. A multilumen manometric catheter according to claim 1 in which:
   said pressure-sensing side openings are positioned along different lines parallel to said longitudinal axis.

4. A multilumen manometric catheter according to claim 1 in which:
   said pressure-sensing side openings are positioned along diametrically opposite lines parallel to said longitudinal axis.

5. A multilumen manometric catheter according to claim 1 in which:
   said pressure-sensing side openings are positioned along four lines parallel to said longitudinal axis, said four lines being circumferentially spaced at substantially 90° apart about the surface of said body.

6. A multilumen manometric catheter according to claim 1 having:
   a rectal balloon surrounding the end of said body distally of said pressure-sensing section; and
   a separate lumen in said body having coupling means at the proximal end of the body for coupling to a pressure source and having an opening at the distal end of the body enabling flow of fluid between said separate lumen and said balloon.

7. A multilumen manometric catheter according to claim 6 in which the distal end of said body extends within said balloon and has a plurality of side openings communicating with said separate lumen to facilitate deflation of the balloon.

8. A multilumen manometric catheter according to claim 1 in which the body has a handle section located proximally of said pressure-sensing section, said handle section comprising an outer tubular member enclosing and supporting said body.

9. A multilumen manometric catheter according to claim 1 in which said body comprises a plurality of tubes, said lumens are the inner open spaces in said tubes, and said tubes are helically oriented about the longitudinal axis of the pressure-sensing section of said body.

10. A multilumen manometric catheter according to claim 9 in which the tubes in at least the pressure-sensing section are adhered to one another to fix the relative positions of said pressure-sensing side openings.

11. A multilumen manometric catheter comprising:
an elongated body comprising a bundle of pressure-sensing tubes having proximal and distal ends extending along a longitudinal axis;
said tubes having pressure transducer coupling means at the proximal ends of the tubes and the distal ends being closed;
said body having a pressure-sensing section in which portions of the tubes are helically wound about said longitudinal axis at the surface of the body;
each of the tubes in the pressure-sensing section having a side opening at the surface of said bundle for sensing pressure of abutting body tissue at that specific location; and
said side openings including at least one group of openings in one quadrant that are positioned along a line parallel to said longitudinal axis at predetermined levels along said axis.

12. A multilumen manometric catheter according to claim 11 having:
an inflatable cuff or balloon surrounding said body;
a central tube having proximal and distal ends extending along said longitudinal axis, having coupling means at the proximal end for coupling to a fluid pressure source, and having an opening communicating with said cuff or balloon to control inflation thereof.

13. A multilumen manometric catheter according to claim 12 in which the helically wound tubes are wound about said central tube in the pressure-sensing section.

14. A multilumen catheter according to claim 12 in which said inflatable cuff or balloon is at the distal end of the body beyond said pressure-sensing section.

* * * * *